(12) United States Patent
Carlton et al.

(10) Patent No.: US 8,298,243 B2
(45) Date of Patent: Oct. 30, 2012

(54) COMBINATION WIRE ELECTRODE AND TUBE ELECTRODE POLYPECTOMY DEVICE

(75) Inventors: John Carlton, Las Vegas, NV (US); Ryan Artale, Boulder, CO (US)

(73) Assignee: Tyco Healthcare Group LP, Mansfield, MA (US)

( * ) Notice: Subject to any disclaimer, the term of this patent is extended or adjusted under 35 U.S.C. 154(b) by 486 days.

(21) Appl. No.: 11/881,847

(22) Filed: Jul. 30, 2007

(65) Prior Publication Data

US 2009/0036899 A1 Feb. 5, 2009

(51) Int. Cl.
*A61B 17/26* (2006.01)

(52) U.S. Cl. ...................................... 606/113

(58) Field of Classification Search .............. 606/37–41, 606/45–52, 110, 113, 127, 114
See application file for complete search history.

(56) References Cited

U.S. PATENT DOCUMENTS

| | | | |
|---|---|---|---|
| 749,689 A | 1/1904 | Houghton |
| 1,952,617 A | 3/1934 | Wappler |
| 1,963,636 A | 6/1934 | Wappler |
| 1,967,015 A | 7/1934 | Wappler |
| 2,002,559 A | 5/1935 | Wappler |
| 2,008,525 A | 7/1935 | Wappler |
| 2,442,966 A | 6/1948 | Wallace |
| 2,532,043 A | 11/1950 | Wallace |
| 3,149,633 A | 9/1964 | Zingale |
| 3,752,159 A | 8/1973 | Wappler |
| 3,856,015 A | 12/1974 | Iglesias |
| 4,011,872 A | 3/1977 | Komiya |
| 4,024,869 A | 5/1977 | Bonnet |
| 4,060,087 A | 11/1977 | Hiltebrandt et al. |
| 4,068,667 A | 1/1978 | Iglesias |
| 4,116,198 A | 9/1978 | Roos |
| 4,134,406 A | 1/1979 | Iglesias |
| 4,202,338 A | 5/1980 | Bitrolf |
| 4,294,254 A | 10/1981 | Chamness |
| 4,311,143 A | 1/1982 | Komiya |
| 4,493,320 A | 1/1985 | Treat |
| 4,503,855 A | 3/1985 | Maslanka |
| 4,718,419 A | 1/1988 | Okada |
| 4,905,691 A | 3/1990 | Rydell |
| 5,066,295 A | 11/1991 | Kozak et al. |
| 5,078,716 A | 1/1992 | Doll |
| 5,158,561 A | 10/1992 | Rydell |
| 5,192,280 A | 3/1993 | Parins |
| 5,197,964 A | 3/1993 | Parins |

(Continued)

FOREIGN PATENT DOCUMENTS

DE EP0035959 A1 * 9/1981

*Primary Examiner* — Ryan Severson
*Assistant Examiner* — Ashley Cronin

(57) ABSTRACT

A device for removing polyps is provided and includes a tubular member having proximal and distal ends. The distal end of the tubular member includes a first electrode extending thereacross. The first electrode defines at least one opening therein. The polyp removal device further includes a snare portion operably extending from within the distal end of the tubular member and through at least one opening defined in the first electrode. The tubular member is configured to deliver electrosurgical energy between the first electrode and the snare portion. The polyp removal device further includes a handle portion operatively extending from within the proximal end of the tubular member. The snare portion may include a second electrode. The snare portion and the first electrode are configured to grasp and seal a polyp therebetween. The first and second electrodes may be independently activated.

20 Claims, 3 Drawing Sheets

U.S. PATENT DOCUMENTS

| | | | |
|---|---|---|---|
| 5,207,686 | A | 5/1993 | Dolgin |
| 5,290,284 | A | 3/1994 | Adair |
| 5,318,564 | A | 6/1994 | Eggers |
| 5,417,697 | A | 5/1995 | Wilk et al. |
| 5,460,629 | A | 10/1995 | Shlain et al. |
| 5,462,553 | A | 10/1995 | Dolgin |
| 5,971,994 | A | 10/1999 | Fritzsch |
| 6,015,415 | A | 1/2000 | Avellanet |
| 6,050,995 | A | 4/2000 | Durgin |
| 6,071,283 | A | 6/2000 | Nardella et al. |
| 6,152,922 | A | 11/2000 | Ouchi |
| 6,235,026 | B1 | 5/2001 | Smith |
| 6,517,539 | B1 | 2/2003 | Smith et al. |
| 6,730,097 | B2 | 5/2004 | Dennis |
| 6,743,228 | B2 | 6/2004 | Lee et al. |
| 6,773,432 | B1 | 8/2004 | Clayman et al. |
| 6,827,717 | B2 | 12/2004 | Brommersma et al. |
| 6,852,108 | B2 | 2/2005 | Barry et al. |
| 6,852,111 | B1 | 2/2005 | Lieber |
| 6,860,848 | B2 | 3/2005 | Wosnitza et al. |
| 6,972,017 | B2 | 12/2005 | Smith et al. |
| 7,008,420 | B2 | 3/2006 | Okada |
| 7,037,307 | B2 | 5/2006 | Dennis |
| 7,104,990 | B2 | 9/2006 | Jenkins et al. |
| 2001/0009985 | A1 | 7/2001 | Durgin et al. |
| 2002/0072739 | A1 | 6/2002 | Lee et al. |
| 2002/0151889 | A1 | 10/2002 | Swanson et al. |
| 2002/0165540 | A1 | 11/2002 | Bales et al. |
| 2003/0009166 | A1 | 1/2003 | Moutafis et al. |
| 2003/0040744 | A1 | 2/2003 | Latterell et al. |
| 2003/0109870 | A1 | 6/2003 | Lee et al. |
| 2003/0114850 | A1 | 6/2003 | McClurken et al. |
| 2003/0125731 | A1 | 7/2003 | Smith et al. |
| 2003/0144661 | A1 | 7/2003 | Brommersma et al. |
| 2003/0153909 | A1 | 8/2003 | Levinson |
| 2003/0176859 | A1 | 9/2003 | Levinson |
| 2003/0181906 | A1 | 9/2003 | Boebel et al. |
| 2003/0204188 | A1 | 10/2003 | Morrison et al. |
| 2003/0212389 | A1 | 11/2003 | Durgin et al. |
| 2003/0216731 | A1 | 11/2003 | Dennis |
| 2004/0064139 | A1 | 4/2004 | Yossepowitch |
| 2004/0097963 | A1* | 5/2004 | Seddon ........................ 606/127 |
| 2004/0106920 | A1 | 6/2004 | Jenkins et al. |
| 2004/0153059 | A1 | 8/2004 | Okada |
| 2004/0199159 | A1 | 10/2004 | Lee et al. |
| 2004/0220564 | A1 | 11/2004 | Ho et al. |
| 2005/0070889 | A1 | 3/2005 | Nobis et al. |
| 2005/0085808 | A1 | 4/2005 | Nakao |
| 2005/0096650 | A1 | 5/2005 | Ouchi |
| 2005/0119652 | A1 | 6/2005 | Vetter et al. |
| 2005/0131402 | A1 | 6/2005 | Ciarrocca et al. |
| 2005/0131403 | A1 | 6/2005 | Chang |
| 2005/0137591 | A1 | 6/2005 | Barry et al. |
| 2005/0171531 | A1 | 8/2005 | Eliachar et al. |
| 2005/0171532 | A1 | 8/2005 | Ciarrocca |
| 2005/0209590 | A1 | 9/2005 | Terakura |
| 2005/0222568 | A1 | 10/2005 | O'Sullivan |
| 2005/0251134 | A1 | 11/2005 | Woloszko |
| 2005/0283150 | A1 | 12/2005 | Moutafis et al. |
| 2006/0009759 | A1 | 1/2006 | Chrisitian et al. |
| 2006/0030846 | A1 | 2/2006 | Buehlmann et al. |
| 2006/0036234 | A1 | 2/2006 | Durgin et al. |
| 2006/0052774 | A1 | 3/2006 | Garrison et al. |
| 2006/0178670 | A1 | 8/2006 | Woloszko et al. |
| 2009/0048591 | A1* | 2/2009 | Ibrahim et al. .................. 606/33 |

* cited by examiner

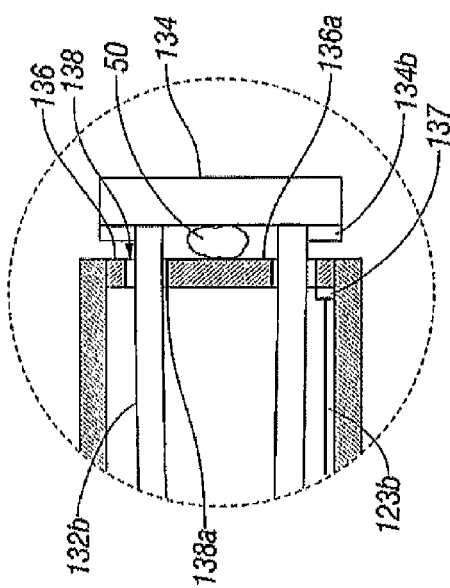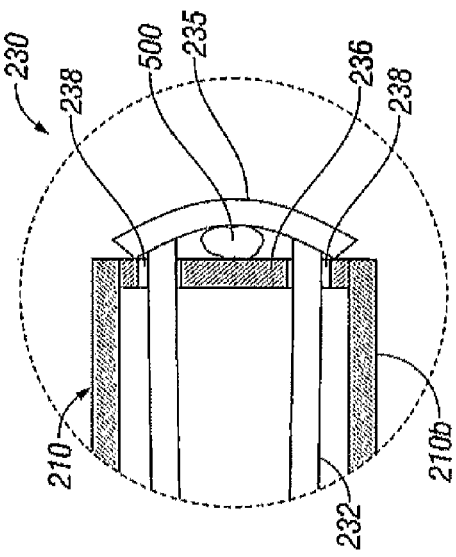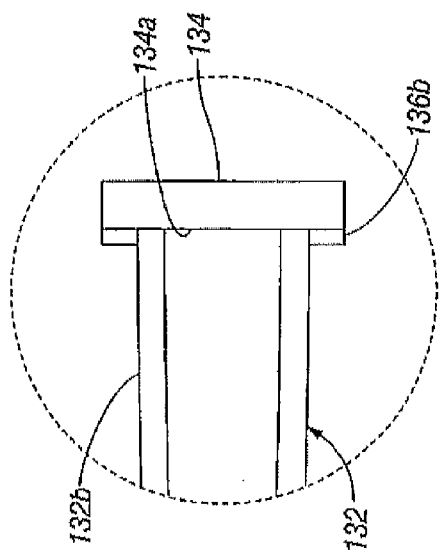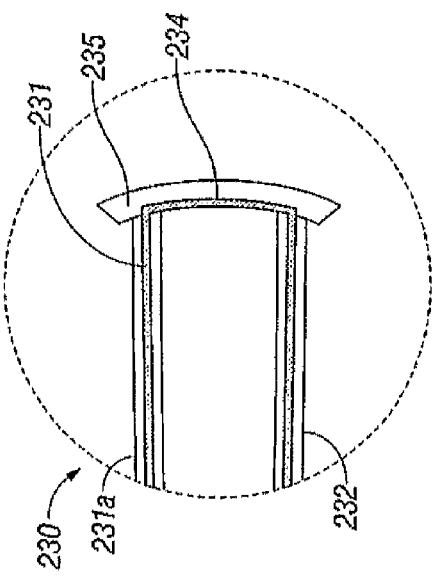

COMBINATION WIRE ELECTRODE AND TUBE ELECTRODE POLYPECTOMY DEVICE

BACKGROUND

1. Technical Field

The present disclosure relates to devices and methods for the removal of internal tissue, and more particularly, to devices including combination wire snare electrode and tube electrode configured for the excision of polyps.

2. Background of Related Art

A polyp is an abnormal growth of tissue projecting from a mucous membrane. A polyp that is attached to the surface of the mucous membrane by a narrow elongated stalk is said to be pedunculated. If no stalk is present, the polyp is said to be sessile. Polyps are commonly found in the colon, stomach, nose, urinary bladder and uterus. Polyps may also occur elsewhere in the body where mucous membranes exist like the cervix and small intestine.

The surgical procedure for removing a polyp is generally referred to as a "polypectomy". Polypectomys are generally endoscopic or laparoscopic procedures performed through the oral or anal cavities. When the location of the polyp permits, the polypectomy may be performed as an open procedure. Conventional polypectomys are completed using various apparatus and techniques known in the art.

As noted above, there are two forms of polyps, sessile and pedunculated. The stalkless or sessile polyps are generally removed using electrical forceps. The excess tissue projecting from the mucous membrane is cauterized, sealed, or the like, and torn from the tissue wall. Pedunculated polyps, or those with stalks, tend to be larger with a greater blood supply. The size and shape of pedunculated polyps typically do not lend themselves to being removed using traditional forceps. Unlike sessile polyps, polyps with a stalk cannot simply be grasped in the jaw members of an electrosurgical forceps and be torn from the tissue wall. Instead, the polypectomy is performed using a surgical snare device.

Conventional snare devices are configured with a snare for looping over the distal end of a hanging polyp and tightening securely around the stalk of the polyp. By constricting the snare, and selectively applying energy to the snare, the device may cauterize or seal the polyp at the stalk as the polyp is severed from the tissue wall. Conventional snare devices may be configured for monopolar or bipolar use. Sealing tissue during a polypectomy using conventional snare devices may require an extended application of energy to the snare to ensure a proper cauterization. This extended application of energy is necessary because of the configuration of the polyp snare and how the snare engages the stalk of the polyp.

SUMMARY

Disclosed is a device configured for removing polyps. In one embodiment, the polyp removal device includes a tubular member having proximal and distal ends. The distal end of the tubular member includes a first electrode extending thereacross. The first electrode defines at least one opening therein. The polyp removal device further includes a snare portion operably extending from within the distal end of the tubular member and through at least one opening defined in the first electrode. The tubular member is configured to deliver electrosurgical energy between the first electrode and the snare portion.

The polyp removal device may further include a handle portion operatively extending from within the proximal end of the tubular member. The handle portion may be configured for operable engagement by a user. The snare portion may include a second electrode. The snare portion and the first electrode are configured to grasp a polyp therebetween. The first and second electrodes may be independently activated.

The snare portion may further include an electrode mounting member configured for operable engagement with the distal end of the tubular member. The snare portion may be configured to be retracted within the tubular member. The snare portion may be retracted within the tubular member upon retraction of the handle portion relative to the base portion. The polyp removal device may further include a generator.

An alternate embodiment of a polyp removal device is disclosed. The polyp removal device includes a tubular member having proximal and distal ends. The distal end may include a first electrode extending across the lumen. The first electrode may define at least one opening therein. The polyp removal device further includes a handle portion operatively extending from the proximal end of said tubular member, and a snare portion slidably supported within the lumen of the tubular member and operably extending from the distal end of the tubular member and through at least one opening defined in the first electrode. At least a section of the snare portion defines a second electrode. The tubular member may be configured to deliver electrosurgical energy to the first and second electrodes. The snare portion of the polyp removal device may be retractable with said tubular member. The first and second electrodes may be independently activated.

Also disclosed is a method of removing a polyp. The method includes the steps of providing a polyp removal device including a tubular member having proximal and distal ends, the distal end including a first electrode extending there across, the first electrode defining one or more openings therein, and a snare portion operably extending from within the distal end of the tubular member and through the one or more openings defined in the first electrode, the tubular member configured for delivering electrosurgical energy through the first electrode; extending the snare portion relative to the tubular member; looping the snare portion about a portion of a polyp; retracting the snare portion relative to the tubular member to ensnare the portion of the polyp; and activating the first electrode.

The snare portion of the polyp removal device may further include a second electrode. The method may further include the step of activating at least one of the first electrode and the second electrode following retraction of the snare portion relative to the tubular member.

BRIEF DESCRIPTION OF THE DRAWINGS

The foregoing summary, as well as the following detailed description will be better understood when read in conjunction with the appended figures. For the purpose of illustrating the present disclosure, a preferred embodiment is shown. It is understood, however, that the present disclosure is not limited to the precise arrangement and instrumentalities shown.

FIGS. 4A and 4B are enlarged partial cross-sectional, top plan views of a snare portion of the polyp removal device of FIGS. 1-3, shown in a first or extended position (FIG. 4A) and in a second or retracted position (FIG. 4B);

FIGS. 5A and 5B are enlarged partial cross-sectional, top plan views of a snare portion of an alternate embodiment of a polyp removal device, in a first or extended position (FIG. 5A) and in a second or retracted position (FIG. 5B);

DETAILED DESCRIPTION OF EMBODIMENTS

Figure 1:
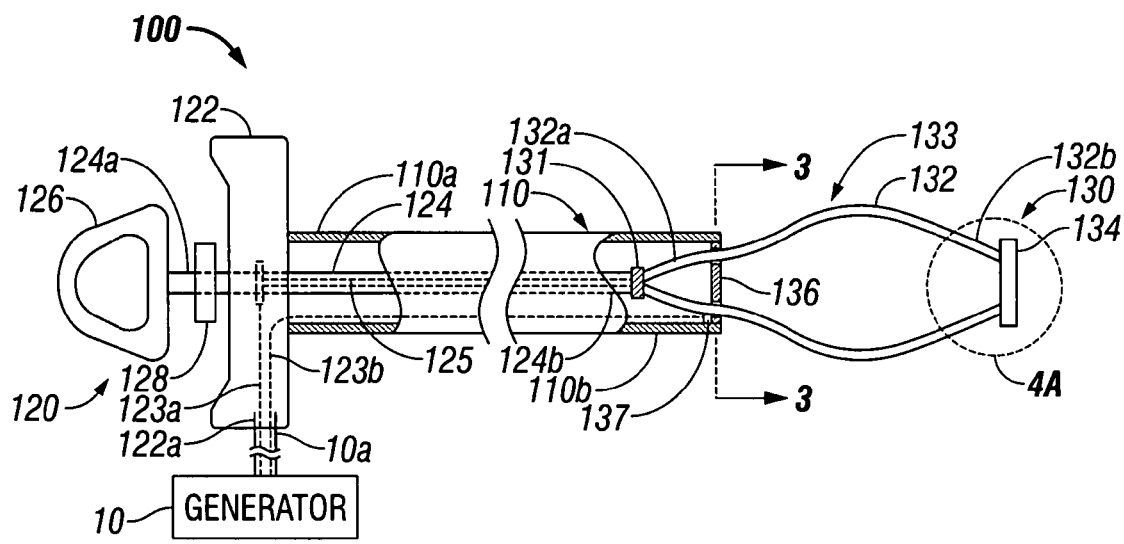
FIG. 1 is a partial cross-sectional, top plan view of a polyp removal device according to an embodiment of the present disclosure, shown in an extended position.

The foregoing summary, as well as the following detailed description will be better understood when read in conjunction with the appended figures. For the purpose of illustrating the present disclosure, various embodiments are shown. It is understood, however, that the present disclosure is not limited to the precise arrangement and instrumentalities shown.

As shown in the drawings and described throughout the following description, as is traditional when referring to relative positioning on an object, the term "proximal" refers to the end of the apparatus which is closer to the user and the term "distal" refers to the end of the apparatus which is further from the user.

Referring to FIGS. 1-4B, an illustrative embodiment of the presently disclosed polyp removal device is shown therein and is generally designated as polyp removal device 100. Polyp removal device 100 includes an elongated tubular member 110, a handle portion 120 extending proximally from tubular member 110, and a snare assembly 130 operably engaged with handle portion 120 and extending distally from within elongated tube 110. Polyp removal device 100 may be of different lengths and sizes for accessing various locations throughout the body. Device 100 may be configured for removal polyps of any size. Preferably, polyp removal device 100 is configured for endoscopic, laparoscopic or translumenal insertion.

Figure 2:
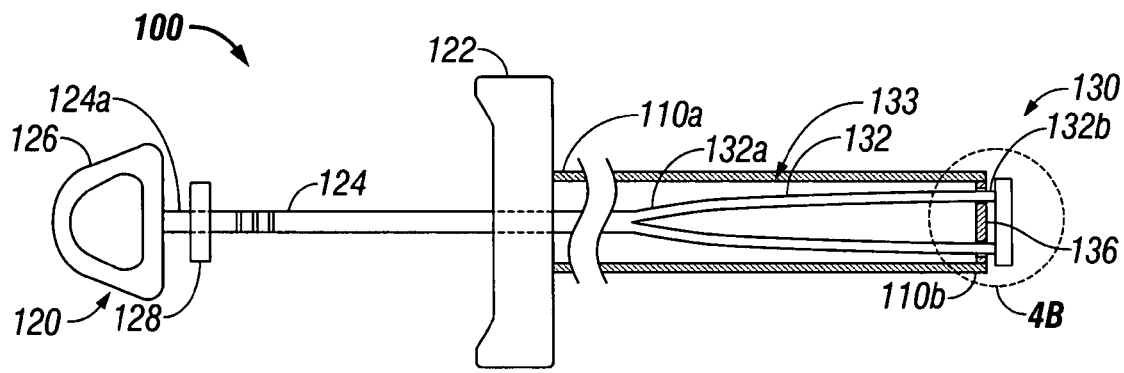
FIG. 2 is a partial cross-sectional top view of the polyp removal device of FIG. 1, shown in a retracted position.

Referring initially to FIGS. 1 and 2, elongated tubular member 110 includes proximal and distal ends 110a, 110b. Proximal end 110a of tubular member 110 is configured for operably engagement with handle portion 120. As will be discussed in further detail below, handle portion 110 may be integrally formed with tubular member 110. Alternatively, handle portion 110 may be releasably secured to tubular member 110, or may instead be securely affixed to tubular member 110. Distal end 110b of tubular member 110 is configured to slidingly receive snare portion 130 therethrough and operably engage electrode 134 when snare 132 is completely retracted therein, as will be described below. Tubular member 110 may be flexible, semi-rigid, or rigid. Tubular member 100 may be constructed of metal, alloy, plastic, polymers or the like.

Still referring to FIGS. 1 and 2, handle portion 120 includes a base 122 securely connected to proximal end 110a of tubular member 110, a connector shaft 124 extending through base 122, and a handle 126 operably connect to a proximal end 124a of connector shaft 124. Base 122 of handle portion 120 may be securely affixed to proximal end 110a of tubular member 110 using adhesive, bonding, mechanical fasteners, welding or similar methods. Alternatively, base 122 may be releasably connected to tubular member 110 using mechanical fasteners, a threaded engagement, friction fitting, a bayonet connection, or the like. In this manner, snare portion 130 may be removed and replaced through proximal end 110a of tubular member 110. Base 122 of handle portion 120 may instead be integrally formed with proximal end 110a of tubular member 110. Handle 126 is configured for operable engagement by a user. Handle 126 may further be knurled or include a coating for facilitating engagement by a user.

Base 122 of handle portion 120 may further be configured for operable engagement with a generator 10. Base 122 may define a connection port 122a for receiving an electrical cord 10a extending from generator 10. First and second wires 123a, 123b extend from connection port 122a through base 122. First wire 123a is operably connected with connector shaft 124, as will be discussed below. Alternatively, first wire 123a may extend through tubular member 110 and operably connect with a first electrode 134 of snare portion 130. Alternatively, first wire 123a may be operably connected with connector shaft 124 independent of base 122. Second wire 123b extends through or along tubular member 110 and is operably connected with an electrode 136 spanning distal end 110b of tubular member 110. Generator 10 may comprise any suitable known generator configured to selectively provide electrosurgical energy to electrodes 134, 136.

Still referring to FIGS. 1 and 2, connector shaft 124 may comprise a single heavy gauge wire. Alternatively, connector shaft 124 may comprise an elongated tubular shaft. Connector shaft 124 includes proximal and distal ends 124a, 124b. Proximal end 124a is configured for operable engagement with handle 126. Handle 126 may be securely affixed, releasable connected, or integrally formed with proximal end 124a of connector shaft 124. Handle 126 is configured for operable engagement by a user. Handle 126 may further be knurled or include a coating for facilitating engagement by a user.

Handle portion 120 may further include a stop member 128 fixedly positioned about connector shaft 124 between base 122 and handle 126. Stop member 128 prevents complete retraction of connector shaft 124 past base 122. Proximal end 124a is further configured to include stop member 128 thereabout. Proximal end 124a may be configured to securely retain stop member 128, or instead, may include grooves or indents 128a for selectively positioning stop member 128 thereabout. In this manner, adjustment of stop member 128 reduces or increases the amount of extension of snare portion 130. Alternatively, stop member 128 may be configured to selectively engaging distal end 124a of connector shaft 124 through the incorporation of a mechanical fastener or the like (not shown).

Distal end 124b of connector shaft 124 is operably connected to snare portion 130. Distal end 124b may be permanently connected, releasably connected or integrally formed with snare portion 130, as will be described below. Connector shaft 124, as shown, is configured for operable engagement with first wire 123a. First wire 123a extends from port 122a and is operably connected with generator 10. As seen in FIG. 1, connector shaft 124 may include a metallic strip or wire 125 extending the length thereof for operably connecting first wire 123a with snare portion 130. Connector shaft 124 maybe constructed of a non-conductive material. Alternatively, connector shaft 124 may be constructed of a conductive material. In this manner, metallic strip or wire 125 would be unnecessary, however, connector shaft 124 would require at least a partial insulative coating to prevent short circuiting of polyp removal device 100. In an alternative embodiment, stop member 128 may be configured for operably engaging first wire 123a.

Referring initially to FIGS. 1 and 2, snare portion 130 includes a snare 132, a first electrode 134 operably connected to snare 132, and a second electrode 136 configured for operable engagement with first electrode 134. Snare 132 defines a substantially flexible hoop 133 having proximal and distal end 132a, 132b. Hoop 133 may be formed as a single, insulated or bare wire. Alternatively, hoop 133 may be formed of a discontinuous wire. Snare 132 may be constructed of one or more bare wires. Alternatively, snare 132 may be insulated to prevent short circuiting of device 100. Proximal end 132a of snare 132 is configured for operable engagement with distal end 124b of connector shaft 124. As discussed above, connector shaft 124 may be permanently connected, releasably connected or integrally formed with snare portion 130. In the event that connector shaft 124 is constructed of a nonconductive material, proximal end 132a of snare 132 may include a junction member 131 for electrically coupling metallic strip 125 formed on connector shaft 124 with snare 132. Snare portion 130 of polyp removal device 100 may be reusable, or in the alternative, may be disposable.

Figure 3:
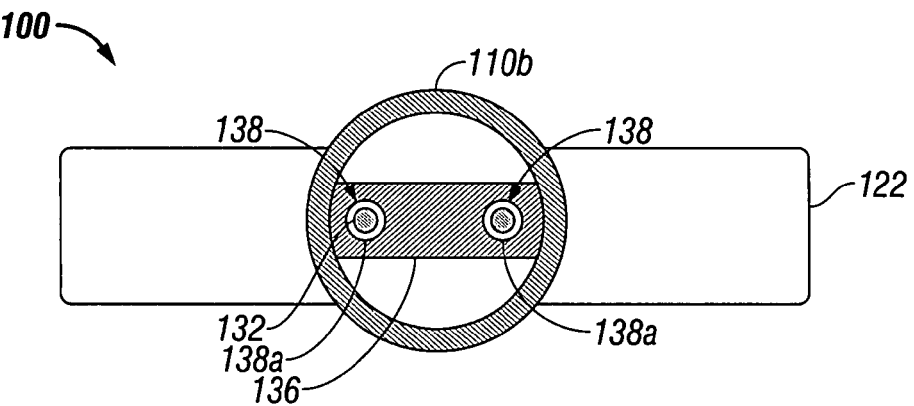
FIG. 3 is a cross-sectional end view of the polyp removal device of FIGS. 1 and 2, taken along line 3-3 of FIG. 1.

Referring now, in particular, to FIG. 3, snare 132 extends through openings 138 formed in second electrode 136. Openings 138 may further include an insulative layer 138a provided therein for preventing a short circuit with snare 132. Second electrode 136 includes a tab 137 (FIG. 1) extending proximally therefrom for operably maintaining a connection between second electrode 136 and second wire 123b. Second electrode 136 spans distal end 110b of tubular member 110. Second electrode 136 may be mounted flush with distal end 110b of tubular member 110, or alternatively, second electrode 136 may be recessed into or extended out of tubular member 110. Second electrode 136 defines a tissue engaging surface 136a (see FIG. 4B) configured for operable engagement with first electrode 134.

Referring now to FIGS. 4A and 4B, distal end 132b of snare 132 includes a first electrode 134. First electrode 134 may form a substantially planar body configured to be operably connect with distal end 132b of snare 132. In an alternate embodiment, first electrode 134 may be removably attached to snare 132. First electrode 134 defines a tissue contacting surface 134a.

In accordance with the present disclosure, by having electrode 136 span distal end 110b of tubular member 110 and having snare 132 extending therethrough, second electrode 136 is configured for better alignment and approximation with first electrode 134. In this manner, tissue engaged between first and second electrodes 134, 136 may be more securely sealed during activation of polyp removal device 100. Additionally, the amount of energy applied to the tissue and the length of time the energy is applied to the tissue may be reduced because of the improved configuration of the present disclosure. Tissue contacting surface 134a may further include one or more stop members 134b configured for preventing contact between tissue contacting surfaces 134a, 136a of first and second electrodes, 134, 136, respectively. Alternatively, a stop member may be formed on second electrode 136.

Referring now to FIGS. 1-2 and 4A-4B, in operation, distal end 110b of tubular member 110 is inserted into a patient. As discussed above, introduction of polyp removal device 100 may be accomplished through an endoscopic or laparoscopic port, or may be inserted translumenally through the mouth or anus. Preferably, snare portion 130 is completely retracted with tubular member 110 during insertion of tubular member 110 into the body. Once distal end 110b of tubular member 110 is positioned near a polyp to be removed, snare 132 of snare portion 130 is extended distally by advancing handle 126 of handle portion 120 relative to base 122 into tubular member 110. In this manner, hoop 133 of snare 132 is opened to receive polyp 50 therethrough.

Once polyp 50 is received within hoop 133 of snare 132, handle 126 of handle portion 120 may be retracted relative to base 122. As handle 126 is retracted, hoop 133 of snare 132 is constricted about polyp 50 until polyp 50 is engaged by tissue engaging surfaces 134a, 136a of first and second electrodes 134, 136, respectively. One or both of electrodes 134, 136 may then be activated to seal, cut, coagulate or severe polyp 50 from the underlying tissue. For purposes of this disclosure, coagulation is defined as a process of desiccating tissue wherein the tissue cells are ruptured and dried, while vessel sealing is the process of liquefying the collagen in the tissue so that it cross-links and reforms into a fused mass.

Referring now to FIGS. 5A and 5B, an alternate snare portion of a polyp removal device 100 is shown generally as snare portion 230. Snare portion 230 is substantially similar to snare portion 130 and will only be described in detail herein to the extent necessary to identify differences in construction and operation. Snare portion 230 includes a snare 232, an electrode mounting member 235 fixedly attached to snare 230, a first electrode 234 operably mounted with electrode mounting member 235, and a second electrode 236 fixedly mounted within a distal end 210b of a tubular member 210. Snare 232 is formed by a wire 231 having an insulative coating 231a provided over at least a portion of a length thereof. Insulative coating 231a prevents wire 231 from shorting as snare 232 is retracted through openings 238 formed in second electrode 236.

With continued reference to FIGS. 5A and 5B, electrode mounting member 235 may be permanently connected, releasably connected or integrally formed with snare 232. Electrode mounting member 235 may be shaped to facilitate insertion into a body cavity. As shown, electrode mounting member 235 includes a rounded or arcuate profile, however, electrode mounting member 235 may be pointed, flat or otherwise suitably configured for insertion into a patient.

Electrode mounting member 235 is configured to operably receive first electrode 234 therein. First electrode 234 may be completely received with electrode mounting member 235. Instead, first electrode 234 may be mounted on or partially received within electrode mounting member 235.

First electrode 234 may be configured to approximate towards second electrode 236 as snare portion 230 is retracted with tubular member 110. In this manner, first and second electrodes 234, 236 operate to grasp a polyp 500 therebetween. Activation of first and/or second electrode 234, 236 may cause sealing, coagulation, cutting, or the like of polyp 500. Electrode mounting member 235 may be configured to prevent first electrode 234 from contacting second electrode 236, as shown (FIG. 5B).

In an alternative embodiment, it is envisioned that tubular member 210 may include one or more electrodes disposed about a distal end thereof configured for operable engagement with first and second electrodes 234, 236. Alternatively, first and/or second electrodes 234, 236 may include a sharpened or serrated edge to facilitate in cutting of tissue.

Figure 6:
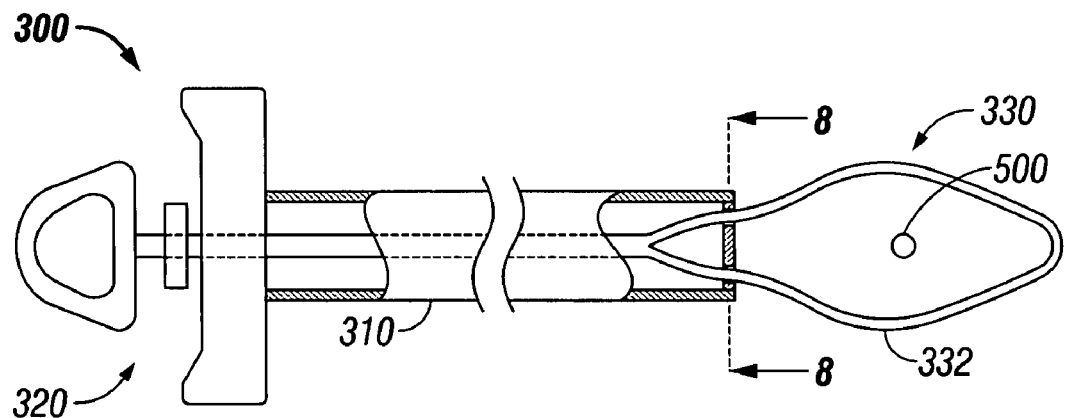
FIG. 6 is a partial cross-sectional, top plan view of a polyp removal device according to another embodiment of the present disclosure, shown in an extended position.
Figure 7:
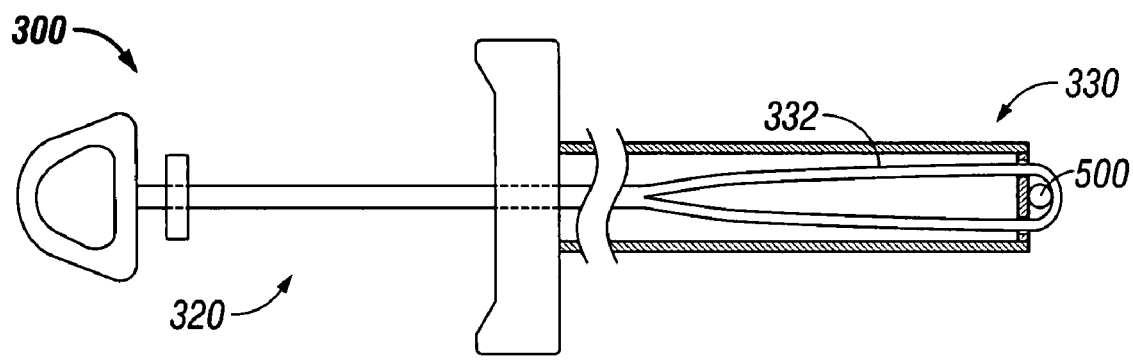
FIG. 7 is a partial cross-sectional top view of the polyp removal device of FIG. 6, shown in a retracted position.
Figure 8:
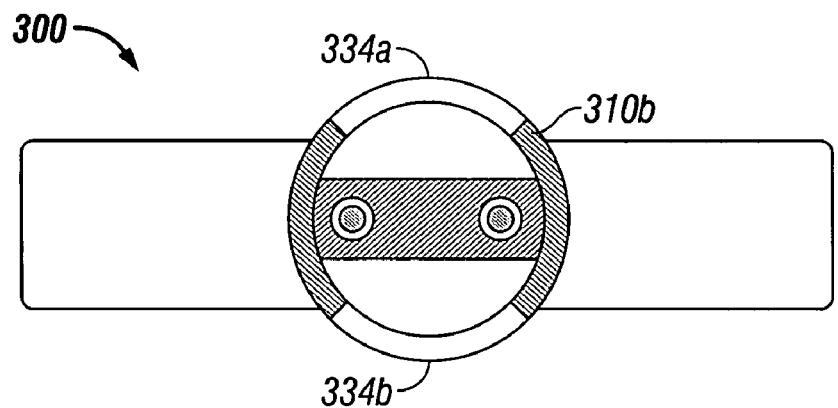
FIG. 8 is a cross-sectional end view of the polyp removal device of FIGS. 6 and 7, taken along line 8-8 of FIG. 6.

Referring now to FIGS. 6-8, illustrated is another embodiment of the present disclosure shown generally as polyp removal device 300. Polyp removal device 300 is substantially similar to polyp removal device 100 disclosed above and will only be described herein to the extent necessary to identify differences therebetween.

Referring initially to FIGS. 6 and 7, polyp removal device 300 includes an elongated tubular member 310, a handle portion 320 extending proximally from tubular member 310, and a snare assembly 330, including snare 332, operably engaged with handle portion 320 and extending distally from within elongated tube 310. Snare 332 is operably connected to a source of electrosurgical energy (not shown). At least a portion of snare 332 is configured to engage and deliver electrosurgical energy to a polyp 500. Turning to FIG. 8, distal end 310b of elongated tube 310 may include one or more electrodes 334a, 334b configured to cooperate with snare 332 to seal polyp 500. Alternatively, all or a portion of elongated tube 310 may form an electrode configured to cooperate with snare 332.

With continued reference to FIGS. 6 and 7, polyp removal device 300 operates in a manner similar to polyp removal device 100 disclosed hereinabove. With snare 332 at least partially disposed within elongated tube 310, distal end 310b of elongated tube 310 is positioned within a body cavity in proximity to a polyp 500 to be removed. Snare 332 is extended from within elongated tube 310 and is looped over polyp 500. Once polyp 500 has been ensnared, snare 332 is retracted within elongated tube 300. As snare 332 is retracted within elongated tube 300, delivery of bipolar electrosurgical energy through snare 332 and one or both of electrodes 334a, 334b begins sealing of polyp 500. Continued retraction of snare 332, coupled with continued application of energy to polyp 500, causes polyp 500 to be completely sealed. Snare assembly 330 may be configured such that complete retraction of snare 332 within elongate tube 310 may severe polyp 500. Alternatively, snare 332 may be extended from within elongated tube 310 and snare 332 removed from about polyp 500. Polyp 500 may then be severed in a conventional manner along the seal made by polyp removal device 300.

Alternate embodiments of polyp removal device 300 are envisioned. Distal end 310b of elongated tube 310 may include serrations or a sharpened surface for severing tissue. Snare 332 may include a serrated or sharpened surface for severing tissue.

Thus, it should be understood that various changes in form, detail and operation of the polyp removal devices of the present disclosure may be made without departing from the spirit and scope of the present disclosure.

What is claimed is:

1. A polyp removal device comprising:
    a tubular member having proximal and distal ends and defining a lumen, said distal end including a first electrode extending across said lumen, said first electrode defining a pair of spaced apart openings therein; and
    a snare portion operably extending from within said distal end of said tubular member and through said pair of spaced apart openings defined in said first electrode, wherein the snare portion is electrically insulated from the first electrode, said tubular member configured for delivering electrosurgical energy between said first electrode and said snare portion.

2. The polyp removal device of claim 1, further comprising a handle portion operatively extending from within said proximal end of said tubular member.

3. The polyp removal device of claim 2 wherein the handle portion is configured for operable engagement by a user.

4. The polyp removal device of claim 2, wherein said snare portion is retracted within said tubular member upon retraction of said handle portion relative to said tubular member.

5. The polyp removal device of claim 1, wherein the snare portion includes a second electrode.

6. The polyp removal device of claim 5, wherein said removal device is configured to grasp a polyp between said first and second electrodes.

7. The polyp removal device of claim 5, wherein said first and second electrodes may be independently activated.

8. The polyp removal device of claim 5, further including an electrosurgical generator.

9. The polyp removal device of claim 8, wherein the electrodes are electrically connected to the electrosurgical generator.

10. The polyp removal device of claim 1, wherein the snare portion and said first electrode are configured to grasp a polyp therebetween.

11. The polyp removal device of claim 1, wherein said snare portion further includes an electrode mounting member configured for operable engagement with said distal end of said tubular member.

12. The polyp removal device of claim 1, further including insulation between said snare portion and said each of said spaced apart openings formed in said first electrode.

13. The polyp removal device of claim 1, wherein said snare portion is configured to be retracted within said tubular member.

14. The polyp removal device of claim 1, wherein the first electrode extends diametrically across said lumen of said tubular member.

15. A polyp removal device comprising:
    a tubular member having proximal and distal ends and defining a lumen, said distal end including a first electrode extending across said lumen, said first electrode defining first and second spaced apart openings therein;
    a handle portion operatively extending from said proximal end of said tubular member; and
    a snare portion slidably supported within said lumen of said tubular member and operably extending from said distal end of said tubular member and through said first and second spaced apart openings defined in said first electrode, wherein at least a section of said snare portion defines a second electrode, the second electrode being electrically insulated from the first electrode, wherein said tubular member is configured to deliver electrosurgical energy to said first and second electrodes.

16. The polyp removal device of claim 15, wherein said snare portion is retractable within said tubular member.

17. The polyp removal device of claim 15, wherein said first and second electrodes may be independently activated.

18. A method of removing a polyp comprising the steps of:
    providing a polyp removal device including:
        a tubular member having proximal and distal ends and defining a lumen, said distal end including a first electrode extending across said lumen, said first electrode defining a pair of spaced apart openings therein; and
        a snare portion operably extending from within said distal end of said tubular member and through said pair of spaced apart openings defined in said first electrode, said tubular member configured for delivering electrosurgical energy through said first electrode independent of delivery of electrosurgical energy to said snare portion;
    extending said snare portion relative to said tubular member;
    looping said snare portion about a portion of a polyp;
    retracting said snare portion relative to said tubular member to ensnare said portion of said polyp; and
    activating said first electrode.

19. The method of claim 18, wherein said snare portion further includes a second electrode.

20. The method of claim 19, further including the step of:
    activating at least one of said first electrode and said second electrode following retraction of said snare portion relative to said tubular member.

* * * * *